(12) United States Patent
Danger et al.

(10) Patent No.: US 7,717,710 B2
(45) Date of Patent: May 18, 2010

(54) CERAMIC INSTRUMENT

(75) Inventors: Karl-Heinz Danger, Detmold (DE); Michael Krumsiek, Lemgo (DE)

(73) Assignee: Gebr. Brasseler GmbH & Co. KG, Lemgo (DE)

( * ) Notice: Subject to any disclaimer, the term of this patent is extended or adjusted under 35 U.S.C. 154(b) by 0 days.

(21) Appl. No.: 10/528,010

(22) PCT Filed: Sep. 10, 2003

(86) PCT No.: PCT/EP03/10051

§ 371 (c)(1),
(2), (4) Date: Nov. 16, 2005

(87) PCT Pub. No.: WO2004/026165

PCT Pub. Date: Jan. 4, 2004

(65) Prior Publication Data

US 2006/0127847 A1    Jun. 15, 2006

(30) Foreign Application Priority Data

Sep. 17, 2002    (DE)    ................ 102 43 104

(51) Int. Cl.
A61C 3/02    (2006.01)
B23B 51/02    (2006.01)

(52) U.S. Cl. ...................... 433/165; 408/227

(58) Field of Classification Search ................ 433/165, 433/166; 408/227
See application file for complete search history.

(56) References Cited

U.S. PATENT DOCUMENTS

| | | | | |
|---|---|---|---|---|
| 4,681,541 A * | 7/1987 | Snaper | ........................ | 433/165 |
| 4,834,655 A * | 5/1989 | Kyotani | ....................... | 433/166 |
| 5,002,439 A * | 3/1991 | Lauder | ......................... | 407/54 |
| 5,096,854 A * | 3/1992 | Saito et al. | ................... | 438/406 |
| 5,201,656 A * | 4/1993 | Sicurelli, Jr. | ................ | 433/166 |
| 5,273,559 A * | 12/1993 | Hammar et al. | ............... | 51/298 |
| 5,369,916 A * | 12/1994 | Jefferies et al. | ............. | 451/532 |
| 5,433,655 A * | 7/1995 | Shiokawa et al. | ............. | 451/48 |
| 5,447,208 A * | 9/1995 | Lund et al. | ................... | 175/428 |
| 5,641,251 A * | 6/1997 | Leins et al. | .................. | 408/144 |
| 5,655,907 A * | 8/1997 | Landgraf | ..................... | 433/165 |
| 5,725,932 A * | 3/1998 | Iio et al. | ...................... | 428/172 |
| 5,858,480 A | 1/1999 | Iio et al. | | |
| 6,319,108 B1* | 11/2001 | Adefris et al. | .............. | 451/533 |
| 6,347,941 B1* | 2/2002 | Boston | ........................ | 433/165 |
| 6,431,800 B1* | 8/2002 | Suzuki | ........................ | 407/119 |
| 6,939,607 B2* | 9/2005 | Kato et al. | ................... | 428/336 |
| 6,986,208 B1* | 1/2006 | Bromer | ........................ | 30/350 |
| 2002/0028422 A1* | 3/2002 | Kumar | ........................ | 433/165 |

(Continued)

FOREIGN PATENT DOCUMENTS

DE    36 00 681 A1    5/1987

(Continued)

Primary Examiner—Ralph A Lewis
(74) Attorney, Agent, or Firm—Pearne & Gordon LLP

(57) ABSTRACT

The present invention relates to a rotating instrument made of a ceramic material and comprising a shaft 1 and a working member 2 which is secured to the shaft or can detachably be secured thereto, wherein at least part of the working member 2 is made from a ceramic material, characterized in that the ceramic part of the working member 2 has a surface roughness of 0.5 µm to 6 µm.

33 Claims, 4 Drawing Sheets

U.S. PATENT DOCUMENTS

2002/0076284 A1 * 6/2002 Kato .................. 407/114

FOREIGN PATENT DOCUMENTS

| DE | 197 03 175 C2 | | 8/1998 |
| --- | --- | --- | --- |
| DE | 198 15 677 C2 | | 10/1999 |
| EP | 0 379 201 | | 7/1990 |
| EP | 0 503 822 | | 9/1992 |
| EP | 0 627 498 | | 12/1994 |
| JP | 02 180517 | | 7/1990 |
| JP | 05309102 A | * | 11/1993 |
| JP | 06 226522 | | 8/1994 |

* cited by examiner

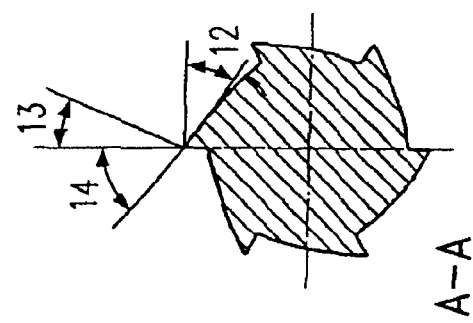
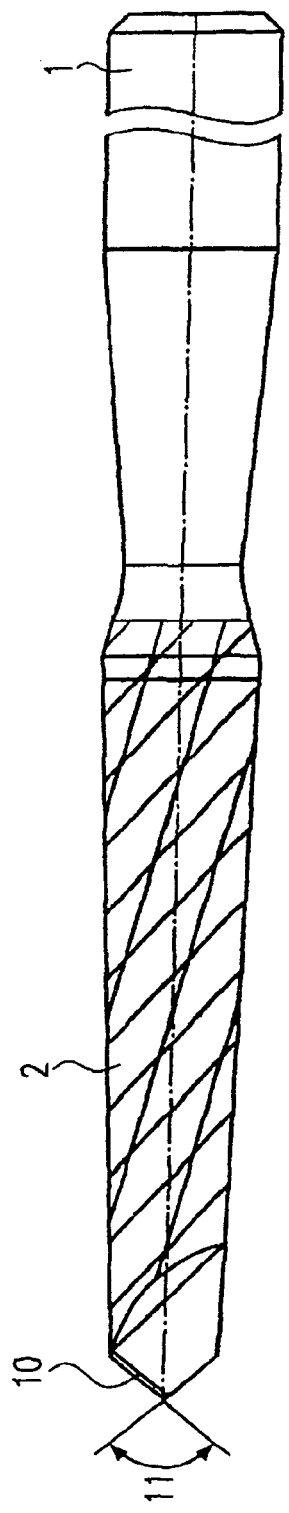
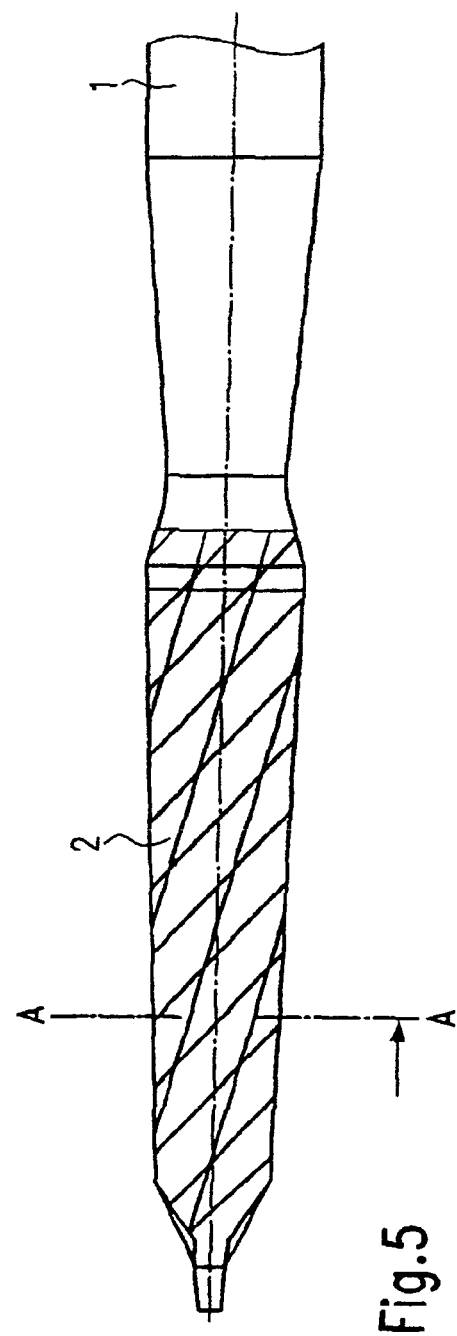

CERAMIC INSTRUMENT

The present invention relates to a rotating instrument according to the preamble of the main claim.

In detail, the present invention relates to a rotating instrument comprising a shaft and a working member which is secured to the shaft or can detachably be secured thereto.

The prior art shows rotating instruments, e.g. dental instruments, drills, surgical saw blades, or the like, which are made from metallic materials. Depending on the respective field of application and the configuration of the rotating instrument, it may turn out to be disadvantageous that metallic wear residues occur in the microrange and are disadvantageous during care or in the later healing process.

The known instruments are e.g. used in the dental field during generation of bone cavities, during treatment of bones or, quite generally, during insertion of implants.

JP 05309102 A shows a dental instrument with a metallic shaft and a ceramic working member. The ceramic working member is here covered with diamond particles which form the cutting edges needed for treatment.

It is the object of the present invention to provide a rotating instrument of the above-mentioned type which while being of a simple construction and producible in an easy and inexpensive way avoids the drawbacks of the prior art and, in particular, has no objectionable influence on the metallic materials.

According to the invention this object is achieved by the features of the main claim; the subclaims show further advantageous designs of the invention.

According to the invention it is thus intended that at least part of the working member of the instrument is made from a ceramic material and has a surface roughness of 0.5 µm to 6 µm. Preferably, the surface roughness may be in the range of 1 µm to 2 µm.

The rotating instrument according to the invention is characterized by a number of considerable advantages. Due to the manufacture of the working member or at least a part thereof from a ceramic material, no problems will arise with respect to metallic wear or metallic residues. Furthermore, any influence on the patient due to direct metallic contact can be excluded.

A further advantage is e.g. also achieved in the case of ceramic veneers in the dental field. Any optical impairment, as is e.g. found in metallic tools or instruments as a dark coloration, does also not arise because metallic wear is prevented. This yields a much better optical overall effect that decisively improves the subsequent treatment or subsequent working steps.

The surface roughness provided according to the invention considerably increases the strength in the case of very small dimensions of dental instruments or surgical instruments. In particular, the occurrence of microcracks, which would lead to breakage and thus to failure of the instrument, is reliably prevented. The rotating instruments of the invention are characterized by a maximum degree of strength despite their small dimensions and their small diameter.

A further measure for increasing the stability and for reducing notch effects consists according to the invention in that all geometrically created form transitions of the ceramic part of the working member have at least radii of 0.01 mm to 5 mm. Preferably, the radii are such that they do not fall below 0.5 mm. This avoids all sharp-edged transitions, e.g. in the case of changes in diameter, during provision of chip flutes, or the like. The indicated radii may also refer to the blank (green compact) of the instruments of the invention, from which the finished instrument is then sintered or burnt. It will be understood by those with ordinary skill in the art that the reference to geometrically created form transitions refers to any line on the ceramic part formed by the intersection of two surfaces at an angle of other than 180°.

A further measure for enhancing the stability of the inventive instruments, which are operated at very high speeds as is e.g. standard in dental drills or the like, consists in providing a core reinforcement which comprises that part of the ceramic portion of the working member that the underlies and is not penetrated by the grooves or cuts in the ceramic portion of the working member. Thus, for example, in FIG. 6, the portion of the ceramic portion of the working member that is shown in cross-section as lying inwardly of the cutting edges or teeth of the ceramic portion of the working member comprises the core reinforcement of the ceramic portion of the working member. This can be created by reducing the depth of grooves or cuts from the free end of the working member to the opposite area of the working member adjoining the shaft. The core reinforcement in that case forms an imaginary conical basic shape that may for example increase at an angle of 0.25° to 3° towards the shaft. A preferred value is in the range of 1°. The conical configuration and the related tapering of the ceramic portion of the working member are shown in FIGS. 4 and 5 of the drawings.

To avoid the occurrence of microcracks, or the like, a microhardening of the structure of the surface of the ceramic part of the working member is intended. The bending strength of the instruments according to the invention can considerably be increased thereby. The microhardening process can be carried out by blasting the surface (by using particles). As will be understood by those of ordinary skill in the art, the microhardness of a surface is a measure of the hardness of the surface as determined by a Vickers or Knoop tester as set forth, for example, in ASTM E-384 and the microhardening of a surface increases the hardness, as measured by a Vickers or Knoop tester. Additionally, increasing the microhardness of the surface of the ceramic portion of the working member will increase its bending strength.

It may be of advantage for protection against wear or for improving the friction properties to provide the surface of the ceramic part of the working member with a hard layer. This layer may e.g. be a TiN layer or a DLC layer.

The use of the ceramic instrument according to the invention is improved by a depth mark. This can be carried out by cut-in grooves which are rounded in the groove bottom (as mentioned above) or by applying a laser. During marking by means of a laser a complete blackening of the area of the ceramic surface to be marked is possible. Alternatively, it is also possible to apply a structure or a geometrical shape which need not be given a surrounding configuration and only creates the impression of a continuous blackening during rotation of the instrument.

The depth mark may e.g. have a surface roughness in the range of 1 µm to 10 µm, a preferred range being 2 µm to 4 µm.

According to the invention it is possible to make the working member and the shaft from the ceramic material. It is possible to join individual ceramic components or also to form the rotating instrument in one piece.

A further advantageous configuration of the invention is that the working member comprises a metallic carrier and at least one layer that is applied thereto and consists of the ceramic workpiece. Instead of the layer, it is also possible to provide an additional ceramic component. The connection may e.g. be established with the help of an adhesive, e.g. by means of a temperature-stable composite.

To make the surface of the ceramic material without pores and to make it smooth, it is advantageous when the surface is ground or polished.

According to the invention it is possible to provide the ceramic material with cutting edges and/or a toothing. It is e.g. possible to configure the instrument of the invention as a saw blade to carry out bone cuts, or the like.

On the whole, the rotating instrument of the invention may be designed as a dental instrument, e.g. as a bone drill or the like. However, it is also possible to design said instrument as a pure grinding or separating tool, e.g. also as a saw blade.

It has turned out to be particularly advantageous when an aluminum oxide and/or a zirconium oxide is/are used as the ceramic material. Mixtures of said two oxides may also be of advantage (e.g. $Al_2O_3$ or $ZrO_2$). Such a mixed ceramic material has excellent properties with respect to the bending strength and toughness. A further variant consists in using zirconium oxide with tetragonal zirconium polycrystals. Such a ceramic material has an even finer grain and thus improved mechanical properties, particularly an increased breaking strength. An improved resistance to aging is accomplished with a corresponding $Al_2O_3$ doping. Such a material shows an excellent biocompatibility.

The instruments of the invention may also be provided with an internal cooling. A continuous drilled hole may e.g. serve this purpose, which hole preferably comprises a plurality of exit openings in the area of the working member of the instrument.

The instrument according to the invention may e.g. be provided with two to three cutting edges, but it is also possible to provide only one cutting edge or a greater number of cutting edges, e.g. four to ten cutting edges.

The toothing (pattern) or grinding of the cutting edges may also be varied. For instance, it is possible to provide a double toothing or cross toothing or a total of three toothings or grindings.

The instrument of the invention may be designed as a drilling or milling instrument; the working member may be configured to be spherical, cylindrical, cylindrical-round, conical, conical-round, stepped or as a thread cutter.

The present invention will now be explained with reference to embodiments taken in conjunction with the drawing, in which:

FIG. 4 is a simplified side view of a further embodiment of an instrument according to the invention in the form of a bone cutter;

FIG. 5 is a side view of the instrument shown in FIG. 4, in an illustration turned by 90°;

FIG. 6 is a sectional view taken along line A-A of FIG. 5;

Figure 1:
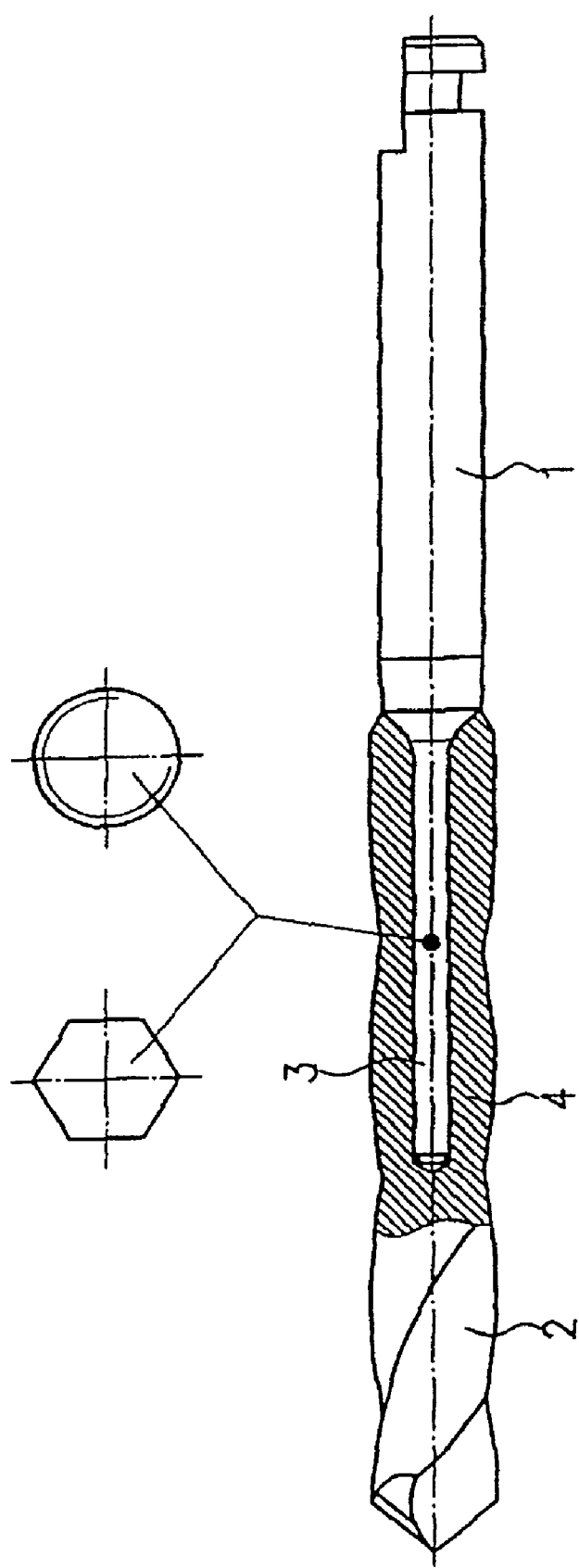
FIG. 1 is a side view, partly in section, of a first embodiment of an instrument according to the invention in the form of a dental drill.

The rotating instrument of the invention as shown in FIG. 1 is configured in the form of a drill. Said drill comprises a shaft 1 having an axis of rotation and a working member 2 which, as is customary with a drill, is provided with cutting edges. The working member 2 need not be illustrated or described in detail because such drills are already known from the prior art.

According to the invention a bolt-like or mandrel-like carrier 3 is secured to the shaft 1 or integrally connected to the shaft 1. The carrier 3 is arranged in a central recess of the working member 2 and thus surrounded by a layer 4 of a ceramic material.

As shown by the detail views of FIG. 1, the carrier 3 may e.g. have a hexagonal cross-section. It may also be provided with a round cross-section which is e.g. equipped with grooves or a thread.

The shaft 1 and the carrier 3 may be made from steel, e.g. from RF steel.

Figure 2:
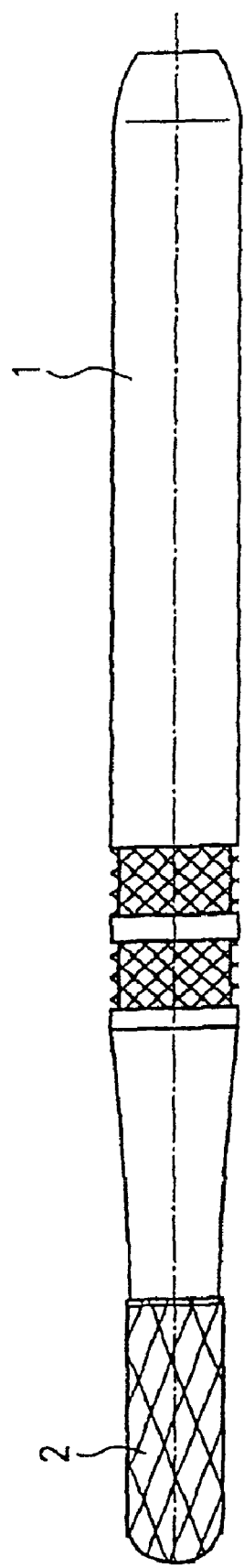
FIG. 2 is a side view of a further embodiment of a dental instrument according to the invention, said instrument being configured in the form of a crown separator.
Figure 3:
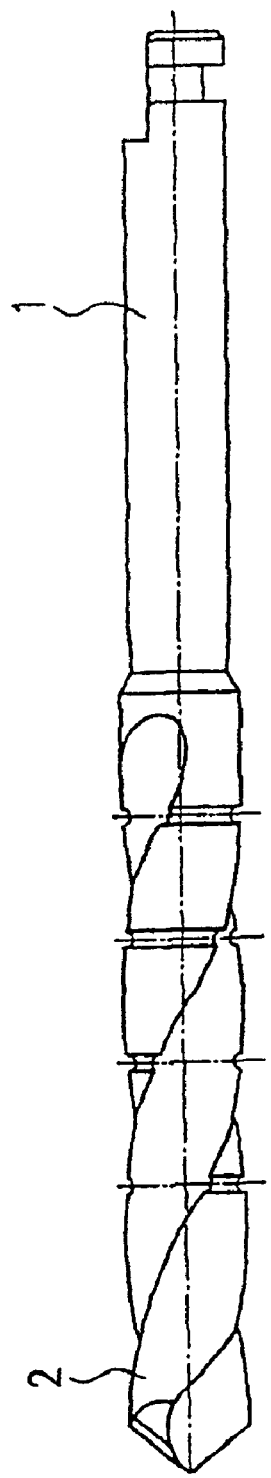
FIG. 3 is a side view of a further embodiment of an instrument according to the invention, said instrument being configured as an implantology pilot drill.

FIGS. 2 and 3 show further embodiments of the rotating instruments of the invention, wherein the working member 2 is each time made from a ceramic material or provided with a layer of a ceramic material. The instrument shown in FIG. 2 is configured in the form of a crown separator whereas the instrument shown in FIG. 3 represents an implantology pilot drill.

FIGS. 4 to 6 show an embodiment in which the instrument of the invention is configured in the form of a bone cutter. The working member 2 may be made integral with the shaft.

Furthermore, the working member 2 comprises crossing cuts or toothings, as shown in FIGS. 4 and 5. The tip of the bone cutter shown in FIGS. 4 and 5 has a clearance cut 10 which may e.g. be 10°. Reference numeral 11 designates a tip angle which may e.g. be 100°. The diameter in the area of the tip may e.g. be 1.44 mm while the length of the working member 2 is 10 mm. The total length of the instrument is e.g. 44.5 mm.

The further dimensions of the instrument may be as follows:
Working partial length: 1-25 mm
Working partial diameter: 1-25 mm
Tip clearance cut: 0-40°
Tip angle: 50-150°
Clearance angle: 0°-70°
Cutting angle: −10°-20°
Twist: 0-80°
Number of teeth: 1-20

A cross toothing with a twist of 20° to 70° is also possible. Likewise, a transverse cut for optimizing the cutting behavior with a pitch of 0.5 of 2.0 mm is also advantageous in a preferred development.

FIG. 6 shows the possible angle once again. It shows, for instance, a clearance angle 12 of 35°. A cutting angle 13 may e.g. be 0° (for better illustration the cutting angle 13 is drawn on an exaggerated scale). A wedge angle 14 is e.g. 50°.

Figure 8:
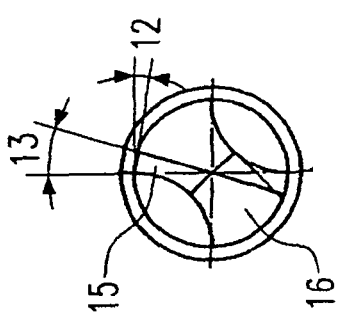
FIG. 8 is a front view of the instrument shown in FIG. 7.
Figure 7:
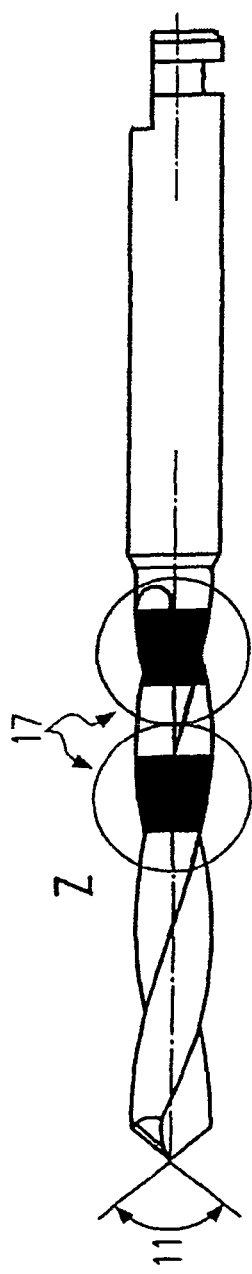
FIG. 7 is a side view of an instrument formed as an implantology pilot drill.
Figure 9:
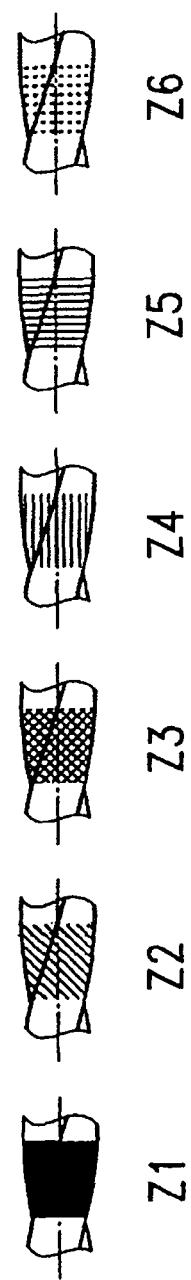
FIG. 9 shows details Z of FIG. 7.

FIGS. 7 to 9 show a further embodiment in which the instrument is configured in the form of an implantology pilot drill. This drill may e.g. have the following dimensions:
Working partial length: 1-25 mm
Working partial diameter: 1-8 mm
Tip clearance cut: 0-40°
Tip angle: 50-150°
Clearance angle: 0-60°
Cutting angle: 0-20°
Twist: 0-60°
Number of teeth: 1-10

FIG. 8 shows, for instance, a cutting angle 13 of 10° and a clearance angle 12 of 8°. Reference numeral 15 designates a clearance cut of the cutting edge which is e.g. 12° whereas reference numeral 16 shows a clearance cut of the cutting edge of 25°.

The implantology pilot drill shown in FIGS. 7 to 9 may be provided with one or several depth marks 17. As shown in FIG. 9, these may have different optical shapes. Detail Z1 shows a complete blackening, detail Z2 an inclined line mark, detail Z3 a cross mark whereas each of details Z4 and Z5 comprises parallel lines. Detail Z6 shows a variant with a point pattern.

The above-described ceramic materials used according to the invention may have the following values:

As illustrated in the various figures of the drawings, the working member (2) of each embodiment is characterized in that the outer surface of the working member is configured, such as for example by the inclusion of flutes, to allow material cut away by the at least one cutting edge and/or toothing to proceed along the outer surface of the working member (2) in a direction that extends generally along the axis of rotation of the shaft (1).

Hardness: 1200-1500
Density: 5.4-6.1
Bending strength: 1200-3000

As indicated above, a means of increasing the stability and reducing notch effects involves providing radii of 0.01 mm to 5 mm, and preferably not less than 0.5 mm, at all geometrically created form transitions of the ceramic part of the working member so as to avoid all sharp-edge transitions such as changes in diameter during the provision of chip flutes or the like. The reference to geometrically created form transitions refers to any line on the ceramic part, other than a cutting edge, that is formed by the intersection of two surfaces at an angle of other than 180°. The foregoing radii may also be applied to the blank (green compact) of the instruments of the invention from which the finished instrument is then sintered or burnt.

Also as indicated above, a further measure for enhancing the stability of the instruments of the invention comprises providing a core reinforcement, the core of the instrument comprising that part of the ceramic portion of the working member that underlies and is not penetrated by the grooves or cuts in the ceramic portion of the working member. The core reinforcement is created by reducing the depth of grooves or cuts from the free end of the working member to the opposite end of the working member adjacent the shaft of the working member. The core reinforcement may increase at an angle of 0.25° to 3°, preferably in the range of 1°, toward the shaft from the free end of the working member.

The occurrence of microcracks and the like can be avoided by microhardening the structure of the surface of the ceramic portion of the working member. The bending strength of the instruments of the invention can be increased as a result. The microhardening process can be carried out by blasting the surface of the ceramic portion of the working member using particles for example. As will be understood by those of ordinary skill in the art, the microhardness of a surface is a measure of the hardness of the surface as determined by a Vickers or Knoop tester as set forth, for example, in ASTM E-384. And the microhardening of a surface increases the hardness of the surface as measured by a Vickers or Knoop tester. Also, increasing the microhardness of the surface of the ceramic portion of the working member can increase its bending strength.

The invention is not limited to the illustrated embodiments. Rather, many alterations and modifications are possible within the scope of the invention.

LIST OF REFERENCE NUMERALS 1 shaft
2 working member
3 carrier
4 layer
10 clearance cut
11 tip angle
12 clearance angle
13 cutting angle
14 wedge angle
15 clearance cut
16 clearance cut
17 depth mark

The invention claimed is:

1. A dental instrument comprising:
a shaft (1); and
a working member (2) which is secured to the shaft, said dental instrument having a longitudinal axis of rotation, said dental instrument being sized and configured to perform a dental procedure in a person's mouth, said dental instrument being sized and configured to rotate at a high speed effective to perform said dental procedure, wherein at least part of the working member (2) is made from a ceramic material, characterized in that at least one cutting edge and/or toothing consisting of the ceramic material is provided in the outer surface of the at least part of the working member (2) that is made from the ceramic material such that the at least one cutting edge and/or toothing consisting of the ceramic material is adapted to perform a cutting function during the dental procedure, wherein the at least part of the working member (2) made from the ceramic material and containing the at least one cutting edge and/or toothing consisting of the ceramic material has a surface roughness of 0.5 μm to 6 μm.

2. The instrument according to claim 1, characterized in that the at least part of the working member (2) made from the ceramic material has a surface roughness of 1 μm to 2 μm.

3. The instrument according to claim 1, characterized in that all geometrically created form transitions of the at least part of the working member (2) made from the ceramic material have radii of at least 0.01 mm to 5 mm.

4. The instrument according to claim 1, characterized in that all geometrically created form transitions of the at least part of the working member (2) made from the ceramic material have radii of at least 0.5 mm.

5. The instrument according to claim 1, characterized in that the working member (2) is provided with a core reinforcement defined by the depth of grooves or cuts made to provide the at least one cutting edge and/or toothing and the depth of the grooves or cuts is reduced from the free end to the shaft of the working member (2).

6. The instrument according to claim 5, characterized in that the core reinforcement has a substantially conical basic shape.

7. The instrument according to claim 5, characterized in that the core diameter increases by 0.25° to 3° towards the shaft.

8. The instrument according to claim 5, characterized in that the core diameter increases by 1° towards the shaft.

9. The instrument according to claim 1, characterized in that the at least part of the working member (2) made from the ceramic material has a microhardened surface.

10. The instrument according to claim 1, characterized in that the surface of the at least part of the working member (2) made from the ceramic material is provided with a hard layer.

11. The instrument according to claim 1, characterized in that the surface of the at least part of the working member (2) made from the ceramic material has a depth mark.

12. The instrument according to claim 11, characterized in that the depth mark has a surface roughness of 1 μm to 10 μm.

13. The instrument according to claim 11, characterized in that the depth mark has a surface roughness of 2 μm to 4 μm.

14. The instrument according to claim 11, characterized in that the depth mark is a laser mark.

15. The instrument according to claim 11, characterized in that the depth mark comprises cut-in grooves.

16. The instrument according to claim 1, characterized in that the entire working member (2) and the entire shaft (1) are made from a ceramic material.

17. The instrument according to claim 1, characterized in that the working member (2) has a metallic carrier (3) and at least one layer (4) that is provided thereon and comprises the at least one part of the working member (2) that is made of the ceramic material.

18. The instrument according to claim 17, characterized in that the layer (4) of the ceramic material is connected to the carrier (3) by means of an adhesive.

19. The instrument according to claim 1, characterized in that the at least part of the working member (2) that is made from the ceramic material has a surface that is free of pores.

20. The instrument according to claim 1, characterized in that the ceramic material comprises aluminum oxide and/or zirconium oxide.

21. The instrument according to claim 1, characterized in that said instrument is a drill.

22. The dental instrument according to claim 1, wherein said working member has a length of 1-25 mm and a diameter of 1-25 mm.

23. The dental instrument according to claim 1, wherein said working member has a diameter of 1-8 mm.

24. The dental instrument according to claim 1, wherein said ceramic material has a density of 5.4 to 6.1 g/cm$^3$.

25. The dental instrument according to claim 1, wherein said working member has a twisted groove for material cut away.

26. The dental instrument according to claim 1, wherein said working member is detachably secured to the shaft.

27. A method of performing a dental procedure comprising the steps of:
(a) providing a dental instrument, said dental instrument comprising a shaft and a working member which is secured to the shaft, said dental instrument having a longitudinal axis of rotation, said dental instrument being sized and configured to perform the dental procedure in a person's mouth, said dental instrument being sized and configured to rotate at a high speed effective to perform the dental procedure, wherein at least part of the working member is made from a ceramic material, characterized in that at least one cutting edge and/or toothing consisting of the ceramic material is provided in the outer surface of the at least part of the working member that is made from the ceramic material such that the at least one cutting edge and/or toothing consisting of the ceramic material is adapted to perform a cutting function during the dental procedure, wherein the at least part of the working member made from the ceramic material and containing the at least one cutting edge and/or toothing consisting of the ceramic material has a surface roughness of 0.5 µm to 6 µm;
(b) rotating said dental instrument about said longitudinal axis of rotation; and
(c) causing said rotating dental instrument to contact tooth or bone and cut said tooth or bone in the course of the dental procedure.

28. The method of claim 27 characterized in that all geometrically created form transitions of the at least part of the working member made from the ceramic material have radii of at least 0.01 mm to 5 mm.

29. The method of claim 27, characterized in that the at least part of the working member made from the ceramic material is provided with a core reinforcement defined by the depth of grooves or cuts made to provide the at least one cutting edge and/or toothing and the depth of the grooves or cuts is reduced from the free end to the shaft of the working member.

30. The method of claim 27, characterized in that the surface of the at least part of the working member made of the ceramic material is microhardened.

31. The method of claim 27, characterized in that the surface of the at least part of the working member made from the ceramic material is provided with a hard layer.

32. The method of claim 27, characterized in that the surface of the at least part of the working member made from the ceramic material has a depth mark.

33. The method of claim 27, characterized in that the dental procedure is selected from the group consisting of the generation of bone cavities, the treatment of bones and the insertion of implants.

* * * * *